US006989036B2

(12) United States Patent
Schröder et al.

(10) Patent No.: US 6,989,036 B2
(45) Date of Patent: Jan. 24, 2006

(54) REACTIVE DYES AND USE THEREOF FOR DYEING SUBSTRATES CONTAINING NUCLEOPHILIC GROUPS

(75) Inventors: Gunter-Rudolf Schröder, Mannheim (DE); Helmut Reichelt, Neustadt (DE); Günther Seybold, Neuhofen (DE); Manfred Patsch, Wachenheim (DE); Stevan David Jones, Guildford (GB); James Charles Dunbar, Morrow, OH (US); Colin John Clarke, Whitton (GB)

(73) Assignee: BASF Aktiengellschaft, Ludwigshafen (DE)

( * ) Notice: Subject to any disclaimer, the term of this patent is extended or adjusted under 35 U.S.C. 154(b) by 71 days.

(21) Appl. No.: 10/473,211

(22) PCT Filed: Apr. 24, 2002

(86) PCT No.: PCT/EP02/04487

§ 371 (c)(1),
(2), (4) Date: Sep. 29, 2003

(87) PCT Pub. No.: WO02/088257

PCT Pub. Date: Nov. 7, 2002

(65) Prior Publication Data

US 2004/0102616 A1    May 27, 2004

(30) Foreign Application Priority Data

Apr. 26, 2001 (DE) ................. 101 20 531

(51) Int. Cl.
*C09B 62/44* (2006.01)
*A61K 7/13* (2006.01)

(52) U.S. Cl. .................. 8/415; 8/428; 564/440; 564/441; 560/8; 562/41

(58) Field of Classification Search ............. 8/435, 8/546, 549, 415, 428; 564/440, 441, 451; 560/8; 562/41, 42
See application file for complete search history.

(56) References Cited

U.S. PATENT DOCUMENTS

| 3,049,393 A | * | 8/1962 | Seemuller ............... 8/415 |
| 3,629,330 A | * | 12/1971 | Brody et al. ............ 564/47 |
| 3,634,478 A | * | 1/1972 | Halasz et al. ........... 558/394 |
| 3,743,678 A | * | 7/1973 | Halasz ................... 564/441 |
| 3,980,535 A | | 9/1976 | Knittel et al. |
| 4,036,825 A | | 7/1977 | Fuchs et al. |
| 4,066,638 A | | 1/1978 | Fuchs et al. |
| 4,102,641 A | | 7/1978 | Tuffile et al. |
| 4,585,460 A | | 4/1986 | Schwander et al. |
| 5,391,718 A | | 2/1995 | Tzikas et al. |

FOREIGN PATENT DOCUMENTS

| DE | 215 4942 | 5/1973 |
| DE | 34 41 273 | 5/1986 |
| EP | 107 614 | 5/1984 |
| EP | 559 617 | 9/1993 |

* cited by examiner

*Primary Examiner*—Margaret Einsmann
(74) *Attorney, Agent, or Firm*—Novak Druce & Quigg LLP

(57) ABSTRACT

The present invention relates to novel reactive dyes of the formula (I)

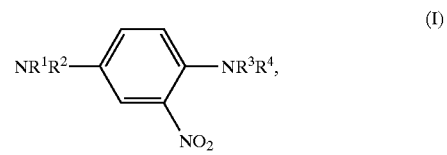

where $R^1$ to $R^4$ are independently hydrogen, $C_1$–$C_8$-alkyl, $C_2$–$C_8$-alkyl, wherein nonadjacent $CH_2$ groups may be replaced by oxygen atoms or imino or $C_1$–$C_4$-alkylimino groups and/or $CH_2$ groups by carbonyl groups, $C_2$–$C_8$-alkenyl, aryl, arylalkylene or a moiety containing a reactive group or the precursor of a reactive group,
with the proviso that at least one of $R^1$ to $R^4$ is a moiety which contains a reactive group or the precursor of a reactive group.

The present invention further relates to the use of the reactive dyes of the formula (I) for dyeing substrates containing nucleophilic groups and to preparations containing at least one reactive dye of the formula (I).

8 Claims, No Drawings

REACTIVE DYES AND USE THEREOF FOR DYEING SUBSTRATES CONTAINING NUCLEOPHILIC GROUPS

The present invention relates to novel reactive dyes of the formula I

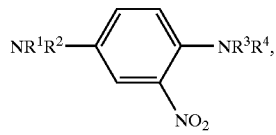

where $R^1$ to $R^4$ are independently hydrogen, $C_1$-$C_8$-alkyl, $C_2$-$C_8$-alkyl, wherein nonadjacent $CH_2$ groups may be replaced by oxygen atoms or imino or $C_1$-$C_4$-alkylimino groups and/or $CH_2$ groups by carbonyl groups, $C_2$-$C_8$-alkenyl, aryl or a moiety containing a reactive group or the precursor of a reactive group, with the proviso that at least one of $R^1$ to $R^4$ is a moiety which contains a reactive group or the precursor of a reactive group.

The present invention further relates to the use of the reactive dyes of the formula I for dyeing substrates containing nucleophilic groups and to preparations containing at least one reactive dye of the formula I.

Reactive dyes have been extensively described for dyeing a wide variety of substrates. For example, the use of reactive dyes for dyeing nitrogenous fibers, such as wool, is known from U.S. Pat. No. 4,066,638, EP 107 614, EP 559 617, DE 34 41 273 and DE 21 54 942.

U.S. Pat. No. 4,102,641 discloses the use of halotriazinyl reactive dyes for dyeing hair.

JP 75 025 529 A recites dye formulations for use as hair dyes. The reactive dyes used therein are based on p-sulfatoethylsulfonylaniline as a diazo component and as a fiber-reactive radical.

It is an object of the present invention to provide further reactive dyes which exhibit good adhesion to the substrates to be dyed and can be applied under gentle dyeing conditions.

We have found that this object is achieved by the reactive dyes of the general formula I described at the beginning.

When $R^1$ to $R^4$ represent radicals having acidic hydrogen atoms, the reactive dyes of the formula I will ordinarily be present in protonated form. But it will be appreciated that the reactive dyes can also occur in the form of their—preferably physiologically acceptable—salts.

In the latter case, suitable cations are derived especially from metal or ammonium ions. Metal ions are especially lithium, sodium or potassium ions. Ammonium ions for the purposes of the present invention are substituted or unsubstituted ammonium cations. Substituted ammonium cations include for example monoalkyl-, dialkyl-, trialkyl-, tetraalkyl- or benzyltrialkyl-ammonium cations or cations derived from nitrogenous five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl is generally straight-chain or branched $C_1$-$C_{20}$-alkyl, which may be substituted by 1 or 2 hydroxyl groups and/or interrupted by 1 to 4 oxygen atoms in ether function.

Useful $C_1$-$C_8$-alkyl for $R^1$ to $R^4$ includes branched or unbranched alkyl chains, for example methyl, ethyl, n-propyl, isopropyl, n-butyl, sec-butyl, isobutyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl or 2-ethylhexyl.

Useful $C_2$-$C_8$-alkenyl for $R^1$ to $R^4$ includes branched or unbranched alkenyl chains, for example vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

$C_2$-$C_8$-Alkyl for $R^1$ to $R^4$ in which nonadjacent $CH_2$ groups may be replaced by oxygen atoms or imino or $C_1$-$C_4$-alkylimino groups and/or $CH_2$ groups by carbonyl groups includes for example
—$(CH_2$—$CH_2$—O—$)_p$H, —$(CH_2$—$CH_2$—O—$)_p$$CH_3$,
—$(CH_2$—$CH(CH_3)$—O—$)_p$H, —$(CH_2$$CH_2$$NR$—$)_p$H,
—$(CH_2$$CH_2$$NR$—$)_p$$CH_3$ or —$(CH_2$$CH(CH_3)$—$NR$—$)_p$H,
where p is 1 or 2, or
—$CH_2$—O—$C(=O)$—$[(CH_2)_r]$H, —$CH_2$$C(=O)$—O—$[(CH_2)_r]$H, —$CH_2$—$NR$—$C(=O)$—$[(CH_2)_r]$H and —$CH_2$—$C(=O)$—$NR$—$[(CH_2)_r]$H, where r is 0, 1, 2, 3, 4 or 5, and R is in each case hydrogen, methyl, ethyl, n-propyl, isopropyl, n-butyl, sec-butyl, isobutyl or tert-butyl.

The last-mentioned formulae include for example the radicals —$CH_2$—O—$C(=O)$—H and —$CH_2$—$C(=O)$—O—H (each with r=0), —$CH_2$$O$—$C(=O)$—$CH_3$ and —$CH_2$$C(=O)$—O—$CH_3$ (each with r=1) and also —$CH_2$—O—$C(=O)$—$C_2H_5$ and —$CH_2$$C(=O)$—O—$C_2H_5$ (each with r=2).

The term aryl is to be understood as meaning for example phenyl, methoxyphenyl or naphthyl or aromatic rings or ring systems having 6 to 18 carbon atoms in the ring system and also up to 24 further carbon atoms which may form further nonaromatic rings or ring systems having 3 to 8 carbon atoms in the ring, which may each be substituted by one or more radicals such as halogen, such as fluorine, chlorine or bromine, cyano, nitro, amino, hydroxyl, alkyl, alkoxy or other radicals. Preference is given to phenyl, p-methoxyphenyl and naphthyl.

Useful arylalkylene radicals include branched-chain or unbranched-chain phenyl-($C_1$-$C_5$-alkylene) or naphthyl-($C_1$-$C_5$-alkylene) radicals such as phenylmethylene, phenylethylene, phenylpropylene, phenyl-1-methylethylene, phenylbutylene, phenyl-1-methylpropylene, phenyl-2-methylpropylene, phenyl-1,1-dimethylethylene, phenylpentylene, phenyl-1-methylbutylene, phenyl-2-methylbutylene, phenyl-3-methylbutylene, phenyl-2,2-dimethylpropylene, phenyl-1-ethylpropylene, naphthylmethylene, naphthylethylene, naphthylpropylene, naphthyl-1-methylethylene, naphthylbutylene, naphthyl-1-methylpropylene, naphthyl-2-methylpropylene, naphthyl-1,1-dimethylethylene, naphthylpentylene, naphthyl-1-methylbutylene, naphthyl-2-methylbutylene, naphthyl-3-methylbutylene, naphthyl-2,2-dimethylpropylene or naphthyl-1-ethylpropylene, and also their isomeric or stereoisomeric forms. Useful aryl radicals include substituted or unsubstituted phenyl or naphthyl radicals. A preferred arylalkylene radical is benzyl.

As to the meaning of $R^1$ to $R^4$ as a moiety containing a reactive group or the precursor of a reactive group, there now follows some remarks. For simplicity, a moiety which contains a reactive group or the precursor of a reactive group is here and hereinafter also referred to by the synonymous "reactive moiety".

Additive reaction of the reactive moieties with the relevant groups in the substrate, for example with the amino groups of hair, means that, for the vinyl sulfone group for example, the amino groups of the hair undergo an addition reaction with the reactive moieties as per the following scheme:

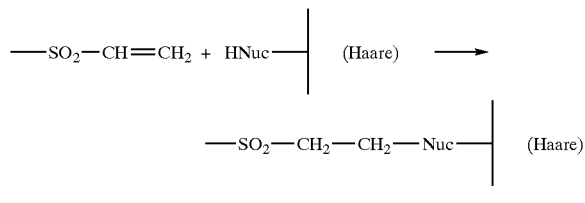

Substitutive reaction of the reactive moieties with the relevant nucleophilic groups (HNuc—) in the substrate, for example with the amino groups of hair, in contrast, means that, for example for the chlorotriazine group, the leaving groups or atoms (chlorine in this case for example) in the reactive moieties are substitutively replaced by the amino groups of the hair as per the following scheme:

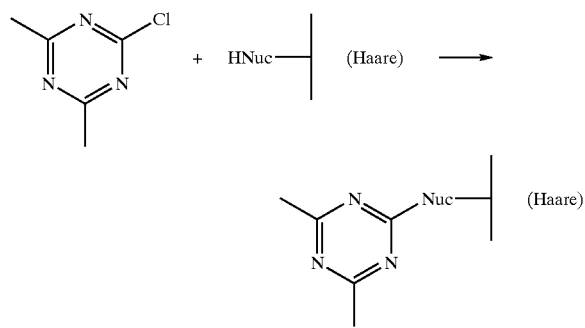

Additively reacting moieties for $R^1$ to $R^4$ include for example acryloyl, mono-, di- or trichloroacryloyl, mono-, di- or tribromoacryloyl, —CO—CCl=CH—COOH, —CO—CH=CCl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2-chloro-2,3,3-trifluorocycloutylcarbonyl, 2,2,3,3-tetrafluorocyclobutylcarbonyl, 2,2,3,3-tetrafluorocyclobutylsulfonyl, 2-(2,2,3,3-tetrafluorocyclobutyl)acryloyl, 1- or 2-alkyl- or 1- or 2-arylsulfonylacryloyl, such as 1-or 2-methylsulfonylacryloyl.

An additively reacting moiety $R^1$ to $R^4$ which contains the precursor of a reactive group is especially —$M^1$-$SO_2$-$C_2H_4Q$, where $M^1$ is phenylene or branched or unbranched $C_1$-$C_8$-alkylene, preferably $C_1$-$C_4$-alkylene, wherein nonadjacent $CH_2$ groups may be replaced by oxygen atoms or imino or $C_1$-$C_4$-alkylimino groups. Examples are $CH_2$, $(CH_2)_2$, $(CH_2)_3$, $(CH_2)_4$, $CH(CH_3)CH_2$, $CH(CH_3)CH(CH_3)$, $(CH_2)_5$, $(CH_2)_6$, $(CH_2)_2O(CH_2)_2$, $(CH_2)_3O(CH_2)_2$, $(CH_2)_2O(CH_2)_2O(CH_2)_2$, $(CH_2)_2NH(CH_2)_2$, $(CH_2)_3NH(CH_2)_2$, $(CH_2)_2NH(CH_2)_2NH(CH_2)_2$,

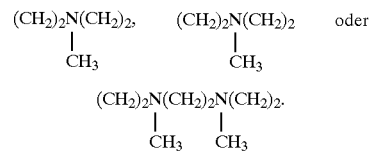

Q is an alkali-detachable group, for example chlorine, bromine, $C_1$-$C_4$-alkylsulfonyl, phenylsulfonyl, $OSO_3H$, $SSO_3H$, $OP(O)(OH)_2$, $C_1$-$C_4$-alkylsulfonyloxy, phenylsulfonyloxy, $C_1$-$C_4$-alkanoyloxy, $C_1$-$C_4$-dialkylamino or a radical of the formula

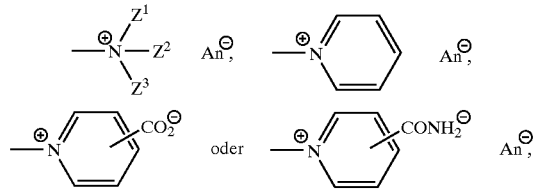

where $Z^1$, $Z^2$ and $Z^3$ are identical or different and each independently represent $C_1$-$C_4$-alkyl or benzyl and each $An^-$ is one equivalent of an anion. Useful anions include for example fluoride, chloride, bromide, iodide, mono-, di- or trichloroacetate, methanesulfonate, benzenesulfonate or 2- or 4-methylbenzenesulfonate.

Q is preferably chlorine, acetate and $SSO_3H$, particularly preferably Q is $OSO_3H$.

A moiety $R^1$ to $R^4$ which contains a reactive group is in particular —$M^1$-$SO_2$-$CH=CH_2$, where $M^1$ is as defined above.

Further additively reacting moieties containing a reactive group or the precursor of a reactive group include for example those of the formulae IIa to IIe, where U is either —$C_2H_4Q$, as defined above, or a vinyl radical.

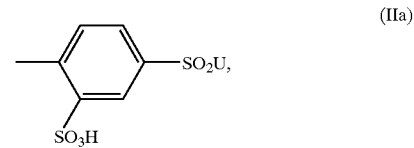
(IIa)

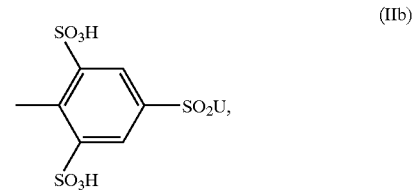
(IIb)

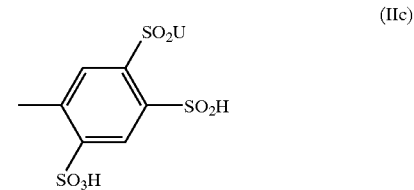
(IIc)

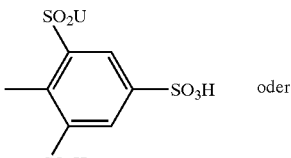

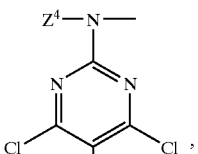, oder

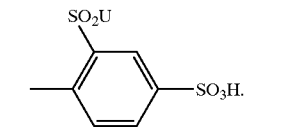

Substitutively reacting moieties for $R^1$ to $R^4$ include for example halogen-substituted radicals derived from 1,3,5-triazine, quinoxaline, phthalazine, pyrimidine, pyridazine or 2-alkylsulfonylbenzothiazole as heterocyclic parent structure.

Of particular suitability in this context are the following heterocyclic radicals which may each contain additively reacting substituents:

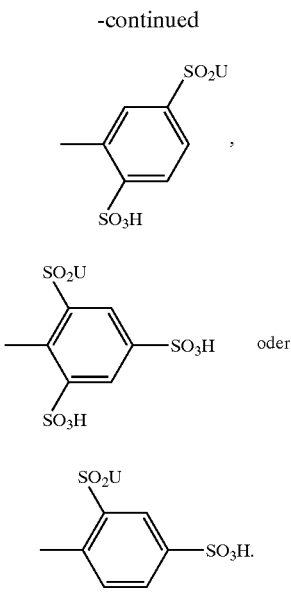

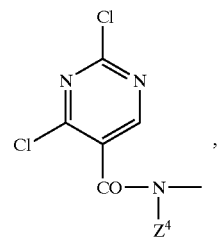

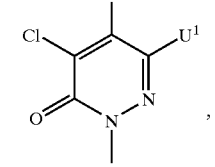

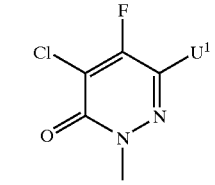

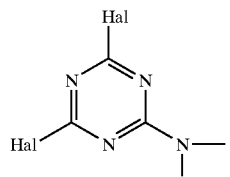

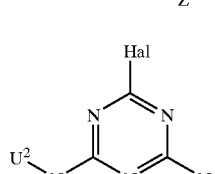

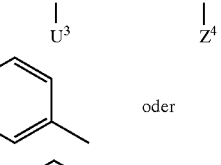

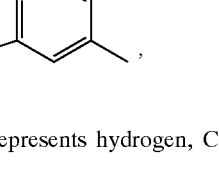

where each $Z^4$ independently represents hydrogen, $C_1$-$C_6$-alkyl or phenyl, Hal is fluorine, chlorine or bromine, $U^1$ is hydrogen or nitro, $U^2$ and $U^3$ are independently hydrogen or $C_1$-$C_6$-alkyl which may be substituted by hydroxyl, halogen, cyano, hydroxysulfonyl or a radical of the formula —$SO_2$-U, in which case U is as defined above, and may be interrupted by 1 or 2 nonadjacent oxygen atoms or imino or $C_1$-$C_4$-alkylimino groups, or $U^2$ and $U^3$ combine with the joining nitrogen atom to form a pyrrolidinyl, piperidinyl, morpholinyl, piperazinyl or N—($C_1$-$C_4$-alkyl)piperazinyl radical, or $U^2$ is a radical of the formula

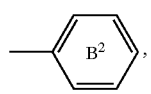

where the rings $B^1$ and $B^2$ may each be singly or doubly hydroxysulfonyl-substituted and/or benzofused and the ring $B^2$ may independently be substituted by one or two substituents selected from the group consisting of chlorine, nitro, $C_1$-$C_4$-alkyl, $C_1$-$C_4$-alkoxy, cyano, carboxyl, acetylamino, hydroxysulfonylmethyl, a radical of the formula $CH_2SO_2U$, a radical of the formula $SO_2U$, a radical of the formula NH—CO—U and a radical of the formula $NU^2$—CO—$NU^2$L—$SO_2U$, where U and $U^2$ are each as defined above and L is $C_2$-$C_6$-alkylene which may be substituted by hydroxyl, chlorine, cyano, carboxyl, $C_1$-$C_4$-alkoxycarbonyl, $C_1$-$C_4$-alkanoyloxy or sulfato and may be interrupted by 1 or 2 nonadjacent oxygen atoms, by 1 or 2 imino groups or by 1 or 2 $C_1$-$C_4$-alkylimino groups. $U^2$ and $U^3$ are each for example methyl, ethyl, propyl, isopropyl, butyl, isobutyl, sec-butyl, tert-butyl, pentyl, isopentyl, neopentyl, tert-pentyl, hexyl or 2-methylpentyl.

$U^2$ and $U^3$ may each also be for example hydroxy-$C_1$-$C_4$-alkyl, such as hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxbut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl or 2-hydroxymethylprop-2-yl.

$U^2$ and $U^3$ may each further be for example cyanomethyl, cyanoethyl, cyanopropyl or cyanobutyl or hydroxysulfonylmethyl, 2-hydroxysulfonylethyl, 2- or 3-hydroxysulfonylpropyl or 2- or 4-hydroxysulfonylbutyl.

L is for example $(CH_2)_2$, $(CH_2)_3$, $(CH_2)_4$, $CH(CH_3)CH_2$, $CH(CH_3)CH(CH_3)$, $(CH_2)_5$ or $(CH_2)_6$.

L may also be for example $(CH_2)_2O(CH_2)_2$, $(CH_2)_3O(CH_2)_2$, $(CH_2)_2O(CH_2)_2O(CH_2)_2$, $(CH_2)_2S(CH_2)_2$, $(CH_2)_3S(CH_2)_2$, $(CH_2)_2S(CH_2)_2S(CH_2)_2$, $(CH_2)_2NH(CH_2)_2$, $(CH_2)_3NH(CH_2)_2$, $(CH_2)_2NH(CH_2)_2NH(CH_2)_2$,

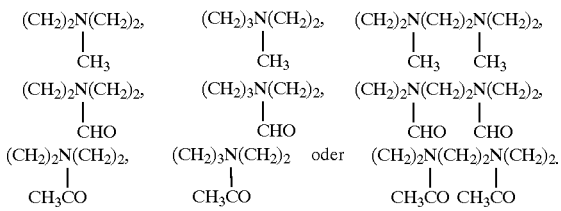

Preferred reactive dyes according to the invention are those wherein the substituents independently have the following meanings:

$R^1$ and $R^2$:
hydrogen, $C_1$-$C_4$-alkyl;
$R^3$: hydrogen;
$R^4$: —$M^1$—$SO_2$—$R^5$;
$M^1$ —$(CH_2)n$—,

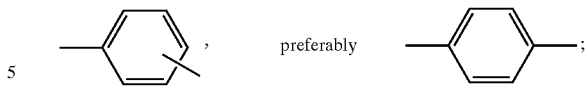

$R^5$: vinyl, —$CH_2$—$CH_2$—$OSO_3H$, —$CH_2$—$CH_2$—O—C (=O)—$R^6$, —$CH_2$—$CH_2$—O—$R^7$;
$R^6$ and $R^7$:
$C_1$-$C_6$-alkyl; and
n: 1 to 4.

Particularly preferred reactive dyes are compounds of the formula I wherein the substituents independently have the following meanings:
$R^1$ and $R^2$:
hydrogen and methyl;
$R^3$: hydrogen;
$R^4$: —$CH_2$—$CH_2$—$SO_2$—CH=$CH_2$, —$CH_2$—$CH_2$—$SO_2$—$CH_2$—$CH_2OSO_3H$.

The present invention further provides for the use of the reactive dyes according to the invention and their preferred embodiments for dyeing substrates containing nucleophilic groups.

Such substrates include for example a very wide variety of styles of cellulose products, for example cotton-based textiles, paper for newspaper and magazine production, pulps for hygiene purposes for example and wood products, for example for furniture making, animal hides, for example leather, and animal furs, but also human skin, for example for the application of temporary tattoos, and human hair.

The reactive dyes according to the invention and their preferred embodiments find preferred use for dyeing substrates containing hydroxyl, mercapto, amino and/or imino groups.

More particularly, the reactive dyes according to the invention and their preferred embodiments find use for dyeing keratinic fibers, specifically animal or human hair.

The present invention also provides preparations containing at least one reactive dye according to the invention.

The reactive dyes according to the invention are customarily applied in dissolved form. For the preferred cosmetic applications, the reactive dyes are dissolved in an aqueous cosmetically acceptable medium. In this aqueous cosmetically acceptable medium, the pH varies between 5 and 9 and is preferably in the range from 6 to 8. It is adjusted to the desired value using mild inorganic or organic bases, salts of weak acids or buffers. Examples are ammonia, ammonium carbonate, potassium carbonate, sodium carbonate, sodium hydroxide, monoethanolamine, diethanolamine, triethanolamine, disodium hydrogenphosphate, sodium citrate and sodium borate.

The reactive dyes are present in the preparations in fractions of from 0.01 to 10% by weight, based on the total weight of the preparation.

Customary assistants in preparations for hair dyeing are anionic, cationic, nonionic or amphoteric surfactants or mixtures thereof. Suitable surfactants are soaps, alkylbenzenesulfonates, alkylnaphthalenesulfonates, sulfates, ether sulfates and sulfonates of fatty alcohols, quaternary ammonium salts, such as trimethylcetylammonium bromide, cetylpyridinium bromide, quaternium 1 to X (INCI), cocoyltrimethylammonium methylsulfate (INCI), hydroxyethylcetyldimomium phosphate (INCI), cetyltrimethylammonium chloride, optionally ethoxylated fatty acid ethanolamides, polyethoxylated acids, alcohols or amines, polyglycerated alcohols, polyethoxylated or polyglycerated alkylphenols and also polyethoxylated alkyl sulfates. Surfactants are present in the compositions of the invention in an amount from 0.5 to 40% by weight, based on the total weight of the preparation.

Further customary assistants are organic solvents as solubilizers, eg. $C_1$–$C_4$-alcohol such as ethanol and isopropanol, glycols, glycol ethers such as ethylene glycol, propylene glycol, 2-methoxyethanol, 2-ethoxyethanol or 2-butoxyethanol, and also glycerol. Solvents are generally present in an amount of 0–40% by weight, based on the total weight of the preparation.

To simplify the handling of the preparations according to the invention, it is customary to add thickeners to them as assistants. Customary thickeners are cellulose derivatives such as methyl-, hydroxymethyl-, hydroxyethyl-, hydroxypropyl- or carboxymethyl-cellulose, sodium alginate, gum arabic, xanthan gum, tragacanth, acrylic acid polymers, polyvinylpyrrolidone, vinyl acetate/crotonic acid copolymers, vinyl acetate/vinylpyrrolidone copolymers, butyl vinyl ether/maleic anhydride copolymers, methyl vinyl ether/maleic anhydride copolymers, or an inorganic thickener such as bentonite. These thickeners are generally used in an amount of up to 5% by weight based on the total weight of the preparation.

Hair cosmetic preparations which are to be used in the form of gels further comprise gel-forming substances such as, for example, carbomers (INCI). For certain caring properties, the preparations may further comprise cationic polymers and silicone compounds. Suitable cationic polymers are, for example, polyquaternium 1 to x (INCI), copolymers of vinylpyrrolidone/vinylimidazolium salts (Luviquat® FC, Luviquats® HM; BASF Aktiengesellschaft, Ludwigshafen), copolymers of vinylpyrrolidone/dimethylaminoethyl methacrylate, quaternized with diethyl sulfate (Luviquat PQ 11); cationic cellulose derivatives (Polyquaternium-4 and 10), acrylamido copolymers (Polyquaternium-7) and cationic guar gum derivatives, eg. guar hydroxypropyltriminium chloride (INCI). Suitable silicone compounds are, for example, polyalkylsiloxanes, polyarylsiloxanes, polyarylalkylsiloxanes, polyethersiloxanes or silicone resins.

Further customary assistants are mild antioxidants which do not react with the dyes, penetrants, sequestrants, buffers, perfume oils, sunscreens (UV-A and UV-B), preservatives, hair-cleaning products and biologically active substances such as panthenol, bisabolol and vitamins, for example of type A, C and E.

The preparations of the invention can be used in liquid form, generally thickened, as cream, paste, as gel or in some other suitable form.

The hair colouring compositions of the present invention may, in addition to the dyes discussed herein above include other nonoxidative, oxidative and other dye materials. Optional nonoxidative and other dyes suitable for use in the hair colouring compositions and processes according to the present invention include demi-permanent, semi-permanent, temporary and other dyes. Non-oxidative dyesas defined herein include the so-called "direct action dyes", metallic dyes, metal chelate dyes, fibre reactive dyes, acid dyes, basic dyes, non-ionic dyes, anionic dyes, cationic dyes, HC dyes and other synthetic and natural dyes.

Oxidative hair colouring agents to be used in the compositions herein are typically, but without intending to be limited thereby, oxidative hair colouring agents, consisting essentially of at least two components, which are collectively referred to as dye forming intermediates (or precursors). Dye forming intermediates can react in the presence of a suitable oxidant to form a coloured molecule. The dye forming intermediates used in oxidative hair colorants include: aromatic diamines, aminophenols, various heterocycles, phenols, naphthols and their various diaminobenzene or its derivatives.

The hair colouring compositions may also comprise at least one oxidising agent, which may be an inorganic or organic oxidising agent.

The oxidising agent is preferably present in the colouring composition at a level of from about 0.01% to about 20%, more preferably from about 0.01% to about 10%, more preferably from about 1% to about 6% by weight of the composition. A preferred oxidising agent for use herein is an inorganic peroxygen oxidising agent.

In a preferred application, a hair cosmetic preparation is applied to the hair, allowed to act for from 5 to 50 minutes, preferably from 10 to 30 minutes, and then the hair is rinsed and, if necessary, washed with a conventional shampoo.

A warm preparation or external heat can be used to speed up the dyeing or deepen the dyeing over the same treatment time. Preference is given to using temperatures within the range from 20 to 40° C.

The reactive dyes of the invention produce uniform dyeings and good coverage of white hair. The dyeings are lightfast, washfast, weatherfast and rubfast.

Furthermore, reactive dyes and their alternative dyeing method make it possible to dispense with $H_2O_2$ as an oxidant in the dyeing process. What is particularly advantageous here is the fact that the hue is predetermined by the dye and not developed on the hair. This simplifies the preparation of dye mixtures and shading.

The examples hereinbelow illustrate the preparation of the compounds according to the invention and the use thereof

PREPARATION EXAMPLE 1 a) Preparation of 2-hydroxyethyl 2'-aminoethyl sulfone:

245 g (2.4 mol) of 96% sulfuric acid were added to 400 g of ice. 484 g (4 mol) of 2-aminoethyl 2'-hydroxyethyl sulfide (J. R. Lotz, B. P. Block, W. C. Fernelius, J. Phys. Chem., 63 (1959), p. 541) were then added dropwise over 30 minutes while the temperature rose to 45° C. This was followed by the addition of 1 g (0.004 mol) of sodium tungstate (Merck) and 10 g of citric acid (Merck), the pH was adjusted to 4.5 with 20% aqueous sodium hydroxide solution and the temperature was raised to 80° C. 953 g (8.4 mol) of 30% hydrogen peroxide solution were added dropwise over 3 hours while the pH was maintained between 4.5 and 5 with 20% aqueous sodium hydroxide solution. Excess peroxide was destroyed with sodium sulfite. The solution was concentrated in a rotary evaporator and was admixed with a total of 1 500 ml of ethanol added a little at a time. Each addition of an ethanol portion was followed by concentrating until finally the remaining oil was made to crystallize by addition of 200 ml of methanol.

This yielded 775 g (3.85 mol) of 2-hydroxyethyl 2'-aminoethyl sulfone.

b) Preparation of N1-(2-(2-sulfatoethylsulfonyl)ethyl)-2-nitrobenzene-1,4-diamine

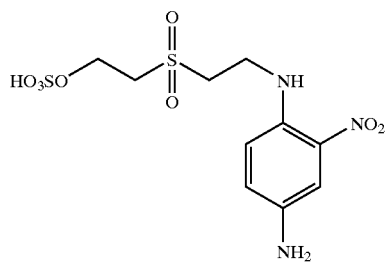

20 g (0.128 mol) of 4-fluoro-3-nitroaniline and 50 g (0.2 mol) of 2-hydroxyethyl 2'-aminoethyl sulfone were stirred up in 100 g of sulfolane and admixed with 24 g of sodium carbonate. The reaction mixture was heated at 100° C. for 8 hours. After cooling to room temperature, 200 ml of concentrated sulfuric acid were added dropwise over an hour. The temperature was kept below 25° C. by external cooling. The reaction mixture was subsequently stirred for one hour and then added gradually to 400 g of ice and 100 g of water. The resultant suspension was admixed with 30 g of sodium acetate and filtered. The filter residue was washed with a little saturated potassium chloride solution and then dried at 30° C. under reduced pressure to leave 30.8 g of the dye (65% of theory) having the above-indicated structure as red crystals. UV: $\lambda_{max}$ (DMF/water 1:1) 498 nm.

DYEING EXAMPLE 1.25 g of the reactive dye of example 1 were dissolved in 25 ml of water and adjusted to pH 7 with sodium hydrogenphosphate. After the solution had been heated to 36° C., a bleached strand of human hair (2 g) was immersed in the solution for 20 minutes at 36° C. The hair was then rinsed with water and air dried. A deep red hair coloration was obtained.

FORMULATION EXAMPLES

A) Hair Dyeing Cream

| Phase I: | |
|---|---|
| 1.5 g | of ceteareth-6 (and) stearyl alcohol (INCI) |
| 1.5 g | of ceteareth-25 |
| 6.0 g | of cetearyl octanoate |
| 3.0 g | of cetearyl alcohol |
| Phase II: | |
| 2 g | of reactive dye of example 1 |
| 2 g | of propylene glycol |
| 84 g | of distilled water |
| q.s. | citric acid/triethanolamine to adjust to pH 7 |
| q.s. | preservative |
| Phase III: | |
| q.s. | perfume oil |

The ingredients were dissolved at 60° C., and then phase I was added to phase II. Phase III was added after cooling to 30° C.

A bleached strand of human hair (2 g) was treated with 0.5 g of the dyeing cream and left for 20 min. It was then rinsed with water, leaving hair dyeing as described in the dyeing example.

B) Hair Dyeing Lotion

| 5 g | of reactive dye of example 1 |
|---|---|
| 1.2 g | of Natrosol ® 250 HR (Aqualon/Hercules Inc. Wilmington, Delaware, USA), (hydroxyethylcellulose to INCI) |
| 1 g | of propylene glycol |
| ad 100 g | of distilled water |
| q.s. | preservative |

A bleached strand of human hair (2 g) was treated with 0.5 g of the dyeing lotion and left for 20 min. It was then rinsed with water, leaving hair dyeing as described in the dyeing example.

C) Hair Dyeing Mousse

| 2 g | of reactive dye of example 1 |
|---|---|
| 3 g | of Luviskol ® VA 64 (BASF Aktiengesellschaft, Ludwigshafen), (PVP/VA copolymer to INCI) |
| 0.45 g | of ceteareth-25 (INCI) |
| 0.10 g | of dimethicone (INCI) |
| 10 g | of propane/butane |
| ad 100 g | of distilled water |
| q.s. | preservative |

A bleached strand of human hair (2 g) was treated with 0.5 g of the hair dyeing mousse, left for 15 min and then rinsed with water. As well as being deeply colored, the hair was very easy to comb through and looked cared-for. The hair dyeing obtained was as described in the dyeing example.

D) Hair Dyeing Shampoo

| 5 g | of reactive dye of example 1 |
|---|---|
| 40 g | of sodium laurylethersulfate to INCI (Texapon ® N 28; Henkel KGaA, Düsseldorf) |
| 10 g | of Tego ® Betain L 7 (Goldschmidt AG/Degussa AG, Düsseldorf) (cocamidopropyl betaine to INCI) |
| 2 g | of Gluatin WQ (wheat germ protein) |
| ad 100 g | of distilled water |
| q.s. | preservative |
| q.s. | sodium chloride as thickener |

The use of a hair dyeing shampoo makes it possible to combine cleaning and dyeing of the hair. A bleached strand of human hair (2 g) was treated with 0.5 g of the hair dyeing shampoo and rinsed out after 1 min until the disappearance of foam. The hair dyeing obtained was as described in the dyeing example.

E) Dyeing Paste

| 2 g | of reactive dye of example 1 |
|---|---|
| 7 g | of titanium dioxide |
| 15 g | of Aerosil (Degussa AG, Düsseldorf) |
| 10 g | of Lutrol ® F 127 (Polyethylene glycol, BASF Aktiengesellschaft, Ludwigshafen) |
| ad 100 g | of distilled water |
| q.s. | preservative |

A bleached strand of human hair (2 g) was treated with 0.5 g of the hair dyeing paste, left for 15 min and then rinsed with water. The hair dyeing obtained was as described in the dyeing example.

F) Hair Dyeing Shampoo

| | |
|---|---|
| 10 g | of reactive dye of example 1 |
| 2.20 g | of xanthan gum (Keltrol ® T; Kelco Biopolymers, San Diego, California, USA) |
| 20.0 g | of sodium laurylethersulfate |
| 2.50 g | of olein diethanolamide |
| 0.10 g | of Trilon ® B (BASF Aktiengesellschaft, Ludwigshafen) |
| ad 100 g | of distilled water |
| q.s. | preservative |

25 g of the dyeing paste were suspended with 25 ml of distilled water, a bleached strand of human hair (2 g) was treated with this dyeing shampoo and left for 20 min. It was then rinsed out with water. The hair dyeing obtained was as described in the dyeing example.

G) Oxidative Hair Colouring Formulation

I. Dye Cream Emulsion

| | |
|---|---|
| q.s. | water |
| 24.75 | emulsion base |
| 4.0 | reactive dye of example 1 |
| 4.125 | 30% aqueous ammonium hydroxide |

II. Emulsion Base Weight % In Use

| | |
|---|---|
| q.s. | water |
| 1.5 | ceteareth 25 |
| 2.25 | cetyl alcohol |
| 2.25 | stearyl alcohol |
| 0.06 | sodium benzoate |
| 0.07 | phenoxyethanol |
| 0.08 | benzyl alcohol |
| 0.02 | tetrasodium EDTA |
| 2.0 | silicone (DC Q2-8220 from Dow Corning) |

III. Hydrogen Peroxide Emulsion Base

| | |
|---|---|
| q.s. | water |
| 4.2 | ceteareth 25 |
| 6.25 | cetyl alcohol |
| 6.25 | stearyl alcohol |

IV. Hydrogen Peroxide Cream

| | |
|---|---|
| 36 | hydrogenperoxide emulsion base |
| 17.7 | 35% hydrogen peroxide |
| q.s. | water |

The dye emulsion base is prepared by a one pot process as follows:
1. Add water to vessel. Heat to above the melt temperature of the fatty alcohols with agitation.
2. Add fatty alcohols and any ethoxylated fatty alcohols, e.g. ceteareth-25, cetyl, stearyl and steareth-2, and allow to melt. Increase agitation.
3. Continue mixing with shear.
4. Beginn cooling with shear adding preservatives at appropriate temperature.
5. During cooling add silicone with mixing until homogeneous.
6. Cool to room temperature.

The hydrogen peroxide cream is also prepared similarly using a one pot process.

All 3 components are thoroughly mixed before application to hair for a 30 minute period, followed by a rinsing with water and dried. A hair colouration as described in the hair colouration example was obtained.

We claim:

1. Reactive dyes of the formula I

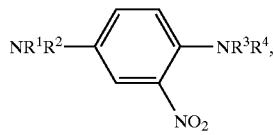

(I)

wherein the substituents independently have the following meanings:

$R^1$ and $R^2$: hydrogen, $C_1$–$C_4$-alkyl;
$R^3$: hydrogen;
$R^4$: —$M^1$—$SO_2$—$R^5$;
$M^1$ —$(CH_2)_n$—,

$R^5$: vinyl, —$CH_2$—$CH_2$—$OSO_3H$, —$CH_2$—$CH_2$—O—$C(=O)$—$R^6$, —$CH_2$—$CH_2$—O—$R^7$;
$R^6$ and $R^7$: $C_1$–$C_6$-alkyl; and
n: 1 to 4.

2. Reactive dyes as claimed in claim 1, wherein the substituents independently have the following meanings:
$R^1$ and $R_2$: hydrogen and methyl;
$R^3$: hydrogen;
$R^4$: —$CH_2$—$CH_2$—$SO_2$—$CH$=$CH_2$, —$CH_2$—$CH_2$—$SO_2$—$CH_2$—$CH_2$—$OSO_3H$.

3. A method for dyeing a substrate containing nucleophilic groups, said method comprising applying a reactive dye as claimed in claim 1 to the substrate.

4. The method of claim 3 wherein the substrate contains hydroxyl, mercapto, amino and/or imino groups.

5. The method of claim 3 wherein the substrate is a keratinic fiber.

6. The method of claim 5 wherein the substrate is an animal or human hair.

7. Preparations containing at least one reactive dye defined as claimed in claim 1.

8. Preparations as claimed in claim 7, comprising hair cosmetic products.

* * * * *